(12) United States Patent
Irion et al.

(10) Patent No.: US 6,390,978 B1
(45) Date of Patent: May 21, 2002

(54) IMAGING METHOD FOR DETERMINING A PHYSICAL OR CHEMICAL CONDITION OF TISSUE IN HUMAN OR ANIMAL BODIES, AND SYSTEM FOR CARRYING OUT THE METHOD

(75) Inventors: Klaus M. Irion, Liptingen; Gerd Beck, Tuttlingen, both of (DE)

(73) Assignee: Karl Storz GmbH & Co. KG (DE)

( * ) Notice: Subject to any disclaimer, the term of this patent is extended or adjusted under 35 U.S.C. 154(b) by 60 days.

(21) Appl. No.: 09/675,402

(22) Filed: Sep. 29, 2000

(30) Foreign Application Priority Data

Oct. 1, 1999 (EP) .............................................. 99119518

(51) Int. Cl.$^7$ ................................................. A61B 8/00
(52) U.S. Cl. ........................ 600/437; 600/439; 600/443; 600/472
(58) Field of Search ................................ 600/437, 407, 600/438–449, 431, 182, 425, 459–467, 472; 606/10, 11, 12, 15–17, 3; 128/898; 73/625, 626; 356/450; 310/335

(56) References Cited

U.S. PATENT DOCUMENTS

| 4,572,201 A | * | 2/1986 | Kondo et al. ............... 310/335 |
| 5,293,873 A | * | 3/1994 | Fang ............................ 600/437 |
| 5,486,170 A | * | 1/1996 | Winston et al. ............. 600/437 |
| 5,573,001 A | * | 11/1996 | Petrosky et al. ............. 600/447 |
| 5,582,171 A | * | 12/1996 | Chornenky et al. ......... 600/425 |
| 6,074,349 A | * | 6/2000 | Crowley ....................... 600/463 |
| 6,210,330 B1 | * | 4/2001 | Tepper ......................... 600/439 |
| 6,210,331 B1 | * | 4/2001 | Raz .............................. 600/443 |
| 6,228,076 B1 | * | 5/2001 | Winston et al. ............. 128/898 |

* cited by examiner

Primary Examiner—Marvin M. Lateef
Assistant Examiner—Ali M. Imam
(74) Attorney, Agent, or Firm—St. Onge Steward Johnston & Reens LLC

(57) ABSTRACT

In an imaging method and a system for determining a physical or chemical condition of tissue in a human or animal body using ultrasound at least one ultrasonic pulse in the diagnostic frequency and power range is injected into the tissue. The ultrasonic echo pulse reflected by the tissue is received and processed in ultrasonographic trace processing means. Further, at least one light beam is generated and split up into at least one measuring light beam and at least one reference light beam. The measuring light beam is injected along the same beam axis along which the ultrasonic pulse is injected into the tissue. The measuring light beam scattered back by the tissue is brought into an interference relationship with the reference light beam and is processed in optical image processing means.

31 Claims, 3 Drawing Sheets

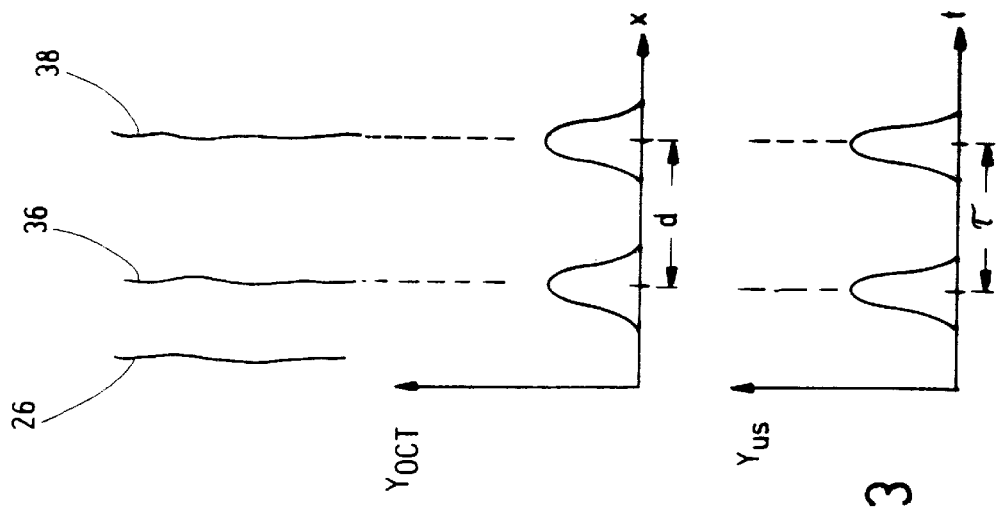
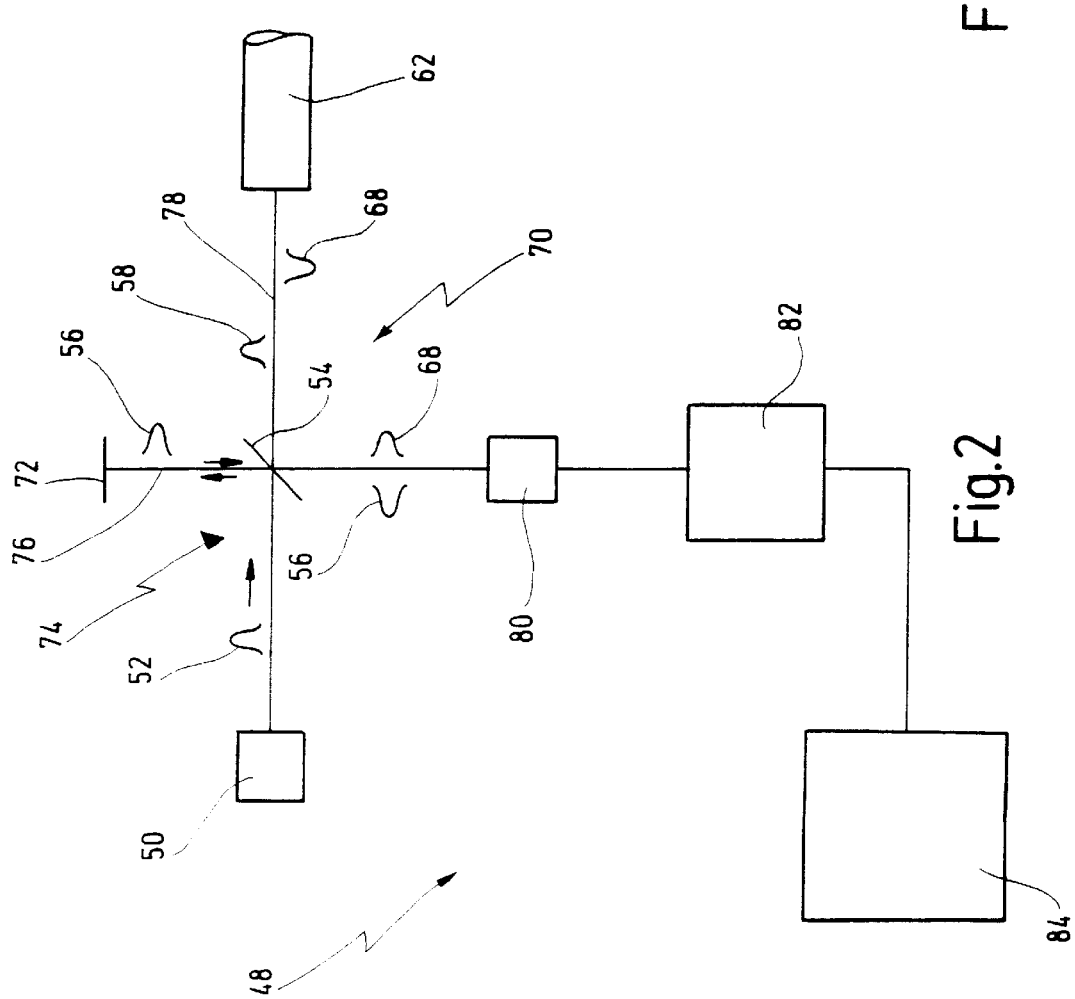
Fig.2
Fig.3

IMAGING METHOD FOR DETERMINING A PHYSICAL OR CHEMICAL CONDITION OF TISSUE IN HUMAN OR ANIMAL BODIES, AND SYSTEM FOR CARRYING OUT THE METHOD

BACKGROUND OF THE INVENTION

The present invention generally relates to an imaging method for determining a physical or chemical condition of tissue in human or animal bodies using ultrasound, where at least one ultrasonic pulse in the diagnostic frequency and power range is directed into the tissue, and the ultrasonic echo pulse reflected by the tissue is received and processed in ultrasonographic image processing means.

The invention further generally relates to an imaging system for determining a physical or chemical condition of tissue in human or animal bodies using ultrasound, having ultrasound-generating means for generating at least one ultrasonic pulse in the diagnostic frequency and power range, ultrasound application means for applying the ultrasonic pulse into the tissue, ultrasound receiving means for receiving the ultrasonic echo pulse reflected in the tissue and ultrasonographic image processing means for processing the ultrasonic echo pulse.

An imaging method of the before-mentioned kind, also known as ultrasonic echo pulse method, and an imaging system of the before-mentioned kind are generally known.

In imaging methods of this kind an electric pulse is converted to an ultrasonic pulse for example by means of a piezoelectric ultrasonic transducer. The electronic pulse is then injected into the tissue under examination. As the ultrasonic pulse enters the tissue, part of it is reflected at the boundary surfaces of the tissue, while part of it penetrates deeper into ion the tissue. Consequently, this method permits several tissue layers, lying one behind the other, to be localized and the condition of those tissue layers to be determined.

Physical condition in the meaning of the present invention is meant to describe, for example, geometrical parameters, such as the extension in space, the position in space, the thickness of the tissue, as well as other physical variables, such as the density of the tissue under examination as a function of the locus. The method is, however, also simply used to describe the visual display of tissue in an image-display unit. The term chemical condition is used, for example, to describe the composition of the tissue.

The ultrasonic echo pulse method allows tissues of organs to be visually displayed and information regarding the tissue to be acquired, it being possible, for example, to determine a pathological condition of the tissue by evaluation of the ultrasonographic image. In order to generate a two-dimensional sectional image a continues sequence of ultrasonic pulses is injected into the tissue through a scanning process which may be of an electronic or mechanical kind.

The advantages of the ultrasonic echo pulse method over the x-ray imaging method lie mainly in the fact that it protects the tissue and can be realized at low cost. Another advantage of the ultrasonic echo pulse method is the relatively great depth of penetration of the ultrasonic pulses into the tissue.

A disadvantage of the ultrasonic echo pulse method lies, however, in the comparatively low axial resolution of the ultrasonographic image. The term axial resolution as used in this connection means the resolution along the axis of irradiation. The resolution along the axis of irradiation is dependent from the frequency and spread of the injected ultrasonic pulse.

At present, standard frequencies in the range of between 5 to 10 MHz are used for the abdominal region. For special tissue structures near the surface, frequencies of up to 50 MHz are already used today. Although such high frequencies achieve improved axial resolution, the attenuation coefficient of the tissue likewise increases linearly with the frequency so that in the case of very high frequencies, which in principle would allow improved resolution, the depth of penetration of the ultrasound into the tissue is heavily limited due to physical reasons so that the advantage of ultrasound, namely that depth information can be obtained about the tissue in a tissue-sparing way, is lost.

The highest possible axial resolution obtainable with high-frequency ultrasound is at present in a range down to 30 $\mu$m.

In WO 97/32182 an optical imaging method is described which is known as "optical coherence tomography (OCT)". With OCT a light beam is generated and splitted up into a measuring light beam and a reference light beam, the measuring light beam being directed into the tissue to be examined. The relative optical path between the reference light beam and the measuring light beam is adjusted, and the measuring light beam scattered back from the tissue is brought to interference with the reference light beam.

In one embodiment in WO 97/32182 an applicator for applying the measuring light beam into the tissue to be examined is described, which is configured in form of an endoscope, in a tip of which a prism or a silver-coated mirror is disposed so that the measuring light beam is injected into the tissue to be examined perpendicular to the longitudinal axis of the endoscope. An ultrasonic transducer is disposed in the tip of the endoscope which directs ultrasonic waves onto the silver-coated mirror which then are injected from the mirror into the tissue to be examined in opposite direction of the measuring light beam.

Further, from WO 98/55025 an ultrasonographic imaging method is known, where it is proposed to combine the ultrasonographic imaging method with optical coherence tomography. In this document, however, it is not described how to carry out the method of optical coherence tomography in connection with an ultrasonographic imaging method.

It is an object of the present invention to improve an imaging method and an imaging system of the type described above so that improved resolution of the imaging method is achieved in order to obtain more precise information about the tissue without losing the depth information.

SUMMARY OF THE INVENTION

According to the present invention, an imaging method for determining a physical or chemical condition of tissue in a human or animal body using ultrasound is provided, comprising the steps of directing at least one ultrasonic pulse in the diagnostic frequency and power range into said tissue along a beam axis, receiving an ultrasonic echo pulse reflected by said tissue, processing said ultrasonic echo pulse in ultrasonographic image processing means, generating at least one light beam and splitting said light beam into at least one measuring light beam and at least one reference light beam, directing said measuring light beam along said beam axis into said tissue, such that said ultrasonic pulse and said measuring light beam are superimposed, adjusting a relative optical path between said reference light beam and said measuring light beam, and bringing said measuring light beam scattered back by said tissue into an interference relationship with said reference light beam and processing the interferometric signal in optical image processing means.

Further, according to the present invention, an imaging system for determining a physical or chemical condition of tissue in a human or animal body using ultrasound is provided, comprising ultrasound-generating means for generating at least one ultrasonic pulse in the diagnostic frequency and poser range, ultrasound application means for applying said ultrasonic pulse into said tissue; ultrasound receiving means for receiving an ultrasonic echo pulse reflected by said tissue, ultrasonographic image processing means for processing said ultrasonic echo pulse, light generating means for generating at least one light beam, beam splitter means for splitting up said light beam into at least one measuring light beam and at least one reference light beam, adjusting means for adjusting a relative optical path between said measuring light beam and said reference light beam, light application means for applying said measuring light beam into said tissue, said light application means and said ultrasound application means being configured such that said ultrasonic pulse and said measuring light beam are superimposed and directed into said tissue along a common beam axis, means for receiving said measuring light beam scattered back by said tissue, means for interferometrically superimposing said back-scattered measuring light beam and said reference light beam, and optical image processing means for processing the interferometric measuring signal.

The invention combines the before-mentioned imaging method using ultrasound with optical coherence tomography, known as such, to an acousto-optical imaging method. For this purpose, the at least one measuring light beam is injected, according to the invention, into the tissue along the same beam axis as the ultrasonic pulse and superimposed therewith. The ultrasound application means and the light application means of the imaging system are correspondingly designed for this purpose for injecting the ultrasound and the light into the tissue along one and the same beam axis.

When the adjustment of the relative optical path between the measuring light beam and the reference light beam is limited to one coherence length, a single image dot is produced. When the optical path is adjusted over a larger area than one coherence length, an initially one-dimensional image is produced in the direction of the injection axis, as the interference signal originates only from the neighborhood of the object spot where identical wavelengths exist between the measuring light beam and the reference light beam. Thus, by adjusting the relative optical path between the measuring light beam and the reference light beam a defined path and/or depth region of the tissue is axially swept in the fashion of a scanning action.

In the context of the invention, the term imaging therefore includes, with respect to the optical path of the measuring method, the generation of an image formed by a one-dimensional sequence of individual image spots. Such an image may, however, also consist of a single image spot. And it is further to be understood that the before-mentioned image processing means is also capable of processing a single measuring signal to produce a single image spot.

The advantages of the method according to the invention, resulting from the combination of the ultrasonic echo pulse method with optical coherence tomography, now lie in the fact that with the aid of optical coherence tomography an axial resolution can be achieved higher than that achievable with the ultrasonic echo pulse method. The resolution achievable with optical coherence tomography is at present in the range of between 5 to 10 $\mu$m. The depth of penetration of the measuring light in the tissue is, however, shorter than the depth of penetration of ultrasound. Thus, it is now possible, with the aid of the method according to the invention, to derive from the received optical high-resolution image information about the tissue from tissue regions near the surface, while additional information on the tissue from deeper tissue regions can be derived from the ultrasonographic image. Especially in the region of axial overlapping between the ultrasonographic image and the optical image it is now possible to acquire information about the tissue useful for the characterization of the tissue, which cannot be obtained with either the ultrasonic echo pulse method or optical coherence tomography alone. So, it is possible, for example, to use the optical image for determining the thickness of a tissue layer, and to thereafter derive from the optically determined thickness of the tissue layer and from the time interval between two ultrasonic echo pulses the ultrasonic speed and from the latter information on the elasticity and density of the tissue. Generally, the ultrasonographic image permits an overview image to be obtained of both the surface of the tissue and the deeper regions. This allows to identify suspicious areas which can then be viewed in detail by optical coherence tomography. To say it in other words, optical coherence tomography, combined with the ultrasonic method, provide a sort of a zoom function.

The method may further be used for therapy control. For example, in skin resurfacing coagulation reinforces the optical interference measuring signal so that the therapy can be stopped at the convenient moment.

The method according to the invention and/or the system according to the invention provide an analytical method that allows to differentiate between tissues and to determine pathological changes in the surface structure of tissue. In addition, dynamic processes, such as flowing blood or motions in the tissue, can be visualized by carrying out the method, for example, in the doppler mode or by generating a rapid sequence of separate images. And finally, functional imaging is also rendered possible. Possible fields of application include, for example, the endoscopic quantification of the cartilage tissue in joints or the endoscopic quantification of the epithelial structures of hollow organs, skin structures being examined, etc.

According to a preferred embodiment of the method, the light beam is generated with a spectral bandwidth in a range of between 10 and 200 nm, and/or with a wavelength in the range of between 600 and 2000 nm.

The light-generating means of the system according to the invention comprise for this purpose a light source with a spectral bandwidth in the range of between 10 and 200 nm, and/or with a wavelength in the range of between 600 and 2000 mm.

The axial resolution of the image acquired by optical coherence tomography increases as the spectral bandwidth increases and/or as the coherence length of the light used decreases. The use of a light source with a great spectral bandwidth thus advantageously results in increased resolution of the optical image obtained, and allows, for example, a geometric parameter to be measured very exactly, or the condition of the tissue to be determined very precisely. The light source used may, for example, be a superluminescent diode with a spectral bandwidth of 30 nm and a power of 1.5 mW.

In a further preferred embodiment the ultrasonic pulse is generated in a frequency range between 1 and 200 MHz and preferably with a bandwidth in the range between 5 and 75 MHz. The ultrasound generation means of the image system according to the present invention are suited to generate ultrasonic pulses in the afore-mentioned parameter ranges, accordingly.

According to another preferred embodiment of the method, the relative optical path between the reference light beam and the measuring light beam is adjusted beyond one coherence length of the light.

Adjusting the relative optical path between the reference light beam and the measuring light beam beyond one coherence length produces, advantageously, at least one one-dimensional optical (depth) image in the direction of irradiation, i.e. the tissue is optically scanned in the direction of irradiation by this measure.

According to a further preferred embodiment of the invention, a sequence of ultrasonic pulses which may be continuous is injected into the tissue as ultrasonic beam, the ultrasonic beam and the measuring light beam being superimposed along the common beam axis.

This feature makes it possible to obtain not only one-dimensional but also two-dimensional sectional images, for example by commonly displacing the ultrasonic beam and the measuring light beam, or by injecting them into the tissue by planar application means. It should be noted at this point that the light beam and, thus, the measuring light beam may also consist of a sequence of light pulses or may be emitted continuously.

In this connection, it is preferred according to the method if the common beam axis of the ultrasonic beam and the measuring light beam are displaced in a plane parallel to the tissue surface.

In the case of this system, further means are provided for displacing the beam axis in a plane parallel to the tissue surface.

This feature makes it possible, with little technical input, to scan the tissue laterally by the ultrasound and the light in order to obtain a two-dimensional ultrasonographic trace/optical sectional image. Other preferred ways of producing two-dimensional sectional images consist in the use of ultrasonic and optical systems, such as arrays, that provide planar images.

It is further preferred in the method if the common beam axis of the ultrasonic beam and of the measuring light beam is rotated about a rotary axis transversely to the instantaneous direction of irradiation.

The system is provided for this purpose with corresponding means for rotating the beam axis about a rotary axis transversely to the instantaneous direction of irradiation.

When embodied in this way, the method and the system are especially well suited for generating ultrasonographic traces/optical sectional images of a hollow organ.

According to a further preferred embodiment of the invention, the image obtained optically by processing the back-scattered measuring light beam and the ultrasonographic image obtained by processing the ultrasonic echo pulse are combined one with the other so that the image obtained by optical means is displayed in the near range and the ultrasonographic trace is displayed in the far range.

In the case of the system, the processing means for the ultrasonographic image and the processing means for the optical image are coupled one with the other in such a way that the ultrasonographic image and the optical image can be displayed one superimposed to the other.

The advantage of this arrangement lies in the fact that a very high resolution can be used in the near range and/or that additional information about the tissue is made available by the ultrasonographic image in the far range. In the case of isolated high-frequency ultrasonographic images, the tissue surfaces mostly cannot be differentiated because strong surface echoes at the transition of the tissue interfere with echoes from slightly deeper structures. The combination with optical coherence tomography according to the invention now permits to achieve high-resolution differentiation of the tissue surface.

According to another preferred embodiment of the method, the thickness of the tissue layer near the surface is determined by means of the optical image obtained by processing the back-scattered measuring light beam, the difference in time delay between the ultrasonic echo pulse reflected at a first tissue layer boundary and the ultrasonic echo pulse reflected at a second tissue layer boundary is determined from the ultrasonographic trace, and the sound propagation speed in the tissue layer is determined from the difference in time delay and the thickness.

As has been mentioned before, the combination, according to the invention, of the ultrasonic echo pulse method and optical coherence tomography opens up new possibilities of determining conditions of the tissue being examined, which heretofore could not be determined with either an ultrasonic imaging method or an optical imaging method alone. The feature described before now permits the elasticity and thickness of the tissue being examined to be determined from the sound propagation speed so determined.

The method and/or the device according to the invention find preferred application, as mentioned before, in tissue differentiation and/or the determination of pathological changes in the surface structure of tissue.

According to a preferred embodiment, the ultrasonographic image is used as overview image of the tissue being examined, while the optical image is used for the detailed imaging of selected tissue regions.

The ultrasonographic method, which provides increased depth of penetration, and optical coherence tomography, which provides improved resolution, can be coupled by suitable image processing methods, especially the merging method, so that after the tissue regions, which possibly might be pathologically changed and must, therefore, be examined more closely, have been identified from a "coarse overview" provided by the ultrasonographic image, details of the tissue being examined can be discerned in the image obtained by optical means.

In addition, as has been mentioned before, the method and the device can be used for therapy control.

According to a further preferred embodiment of the method, fluorescence is additionally induced in the tissue by the measuring light beam or light irradiated into the tissue independently of the light beam, and the fluorescent light is received, and the fluorescent image is displayed in addition to the image obtained by optical means.

In the case of this embodiment of the method according to the invention, the method is combined with what is known as photodynamic diagnosis (PDD). In photodynamic diagnosis, fluorescence is induced, in some instances after administration of a light-sensitive substance into the tissue, which fluorescence can then be used for further differentiation, especially for differentiating between healthy tissue and pathologically changed tissue. For producing surface or sectional images, use can be made in this case either of endogenous autofluorescence or, as has been mentioned before, of xenofluorescence induced by administered drugs. The images so obtained can be used for identifying suspicious areas and also as support for and/or in supplementation of the information gained from the ultrasonographic image and the optical image, for further differentiation.

The method of optical coherence tomography can be combined with photodynamic diagnosis also without the ultrasonographic method, although the combination of ultrasonographic image, optical coherence tomography and photodynamic diagnosis is described as being advantageous in the present specification.

According to a further preferred embodiment of the system, the ultrasound application means and the light application means are both integrated in an applicator designed as endoscope.

An endoscopic applicator is especially well suited for endoscopically quantifying the cartilage tissue, for example in joints, and for endoscopically quantifying the epithelial structures of hollow organs.

It is further preferred in this connection if the ultrasound generation means comprise at least one piezoelectric ultrasonographic transducer and the light applicator means comprise at least one light pipe ending substantially centrally in a radiation surface of the ultrasonic transducer.

Implementing the system with an endoscopic applicator provides the advantage that only one applicator system must be used and no additional deflection systems are required for injecting the ultrasonic beam and the light beam into the tissue along the same beam axis.

According to a further preferred embodiment, the light application means and the ultrasound application means comprise a mirror arrangement that is permeable to ultrasound and reflecting to light, or vice versa, in order to inject the ultrasonic pulse and the measuring light beam along the common beam axis.

This feature provides the advantage that existing applicators, namely on the one hand a separate ultrasound applicator and on the other hand a separate light applicator, can be used, the ultrasonic beam and the light beam being then superimposed by means of the mirror arrangement so that both beams can be injected into the tissue along the same beam axis.

According to a further preferred embodiment the beam splitter means and the means for interferometrically superimposing the back-scattered measuring light beam and the reference light beam comprise a single-beam or multiple-beam interferometer, preferably a Michelson interferometer.

The use of a single-beam or a multiple-beam interferometer, preferably a Michelson interferometer, has proven its value in optical coherence tomography and can be implemented equally in the system according to the invention, at especially low cost, for example as part of an optical driving and evaluation unit.

Further advantages are evident from the description below and the appended drawings.

It is understood that the features recited above and those yet to be explained below can be used not only in the respective combination indicated, but also in other combinations or in isolation, without leaving the context of the present invention.

BRIEF DESCRIPTION OF THE DRAWINGS

Exemplary embodiments of the invention are shown in the drawings and will be explained in more detail in the description below. In the drawings:

FIG. 2 shows a diagrammatic view of part of the system of FIG. 1;

FIG. 3 shows a diagram illustrating the determination, by way of example, of a geometrical parameter of the tissue;

DETAILED DESCRIPTION OF PREFERRED EMBODIMENTS

Figure 1:
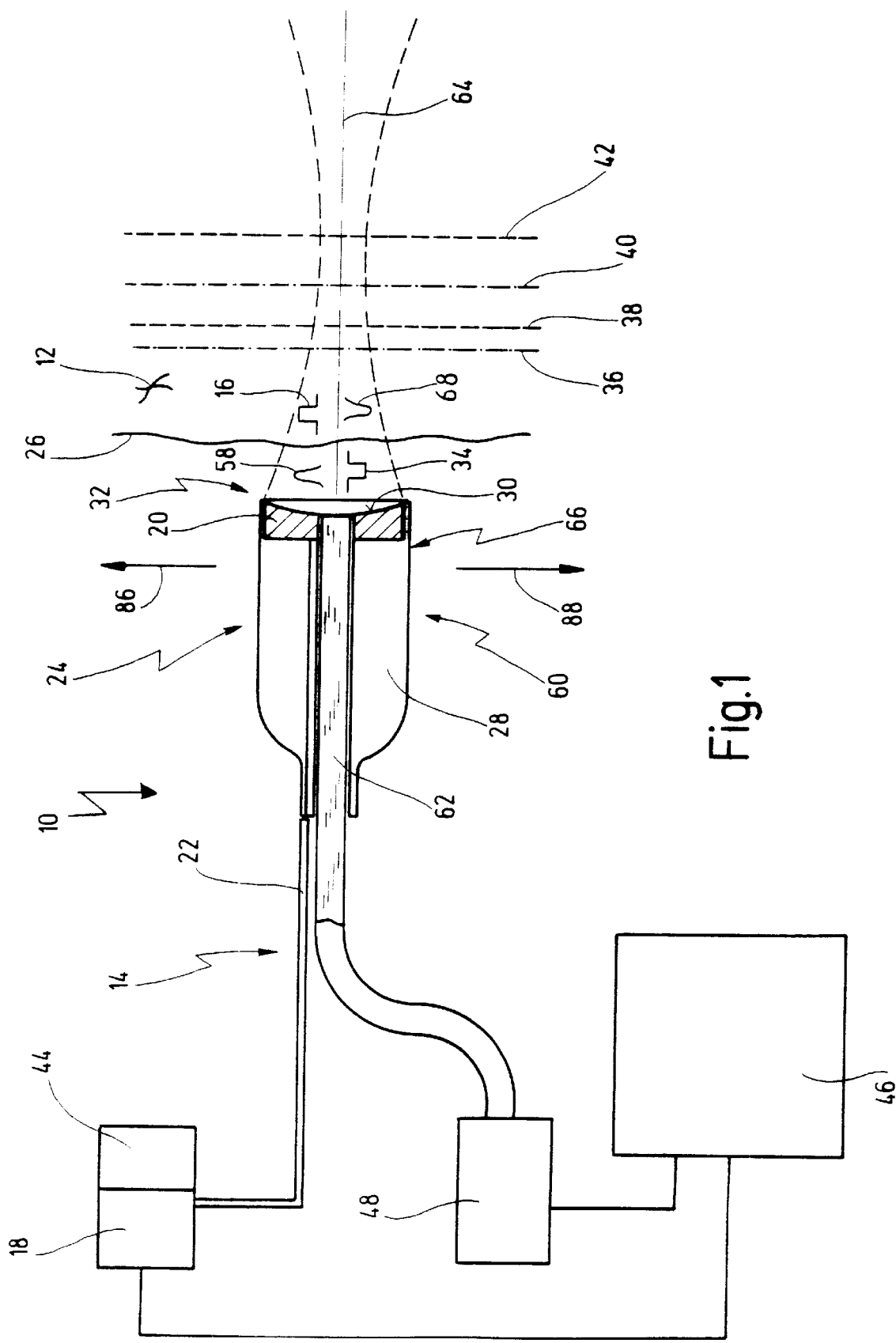
FIG. 1 shows a very diagrammatic overall view, partly sectioned in lengthwise direction, of an imaging system according to the invention for determining a physical or chemical condition of tissue in a human or animal body.

FIGS. 1 and 2 show an imaging system, indicated generally by reference numeral 10, for determining a physical or chemical condition of tissue 12 in a human or animal body using ultrasound.

The imaging system 10 is used for carrying out an imaging method intended for the differentiation of tissue and/or for determining pathological changes of the tissue 12, by determining a physical or chemical condition, for example one or more geometrical parameters of the tissue, which process may also be understood simply as the visual representation of the tissue on a display unit.

The tissue 12 is, for example, skin tissue, cartilage tissue, or the like.

The system 10 comprises on the one hand ultrasound generation means 14 for generating at least one ultrasonic pulse 16.

The ultrasound generation means 14 comprise a pulse generator 18 that produces at least one electric pulse. The ultrasound generation means 14 further comprise a piezoelectric ultrasonic transducer 20. The ultrasonic transducer 20 is connected to the pulse generator 18 via an electric line 22.

The electric pulse generated by the pulse generator 18 is supplied, via the line 22, to the ultrasonic transducer 20 where the electric pulse is converted to an ultrasonic pulse 16.

Usually, a continuous sequence of electric pulses is generated in the pulse generator 18 and, correspondingly, a continuous sequence of ultrasonic pulses 16 is generated by the ultrasonic transducer 20.

The ultrasonic pulses 16 generated by the ultrasound generation means 14, or more precisely by the ultrasonic transducer 20, have a frequency and power in the diagnostic range. Ultrasound frequencies in the diagnostic range lie approximately in a range of between 10 and 50 MHz, generally in the range between 1 and 200 MHz with a bandwidth in the range between 1 and 75 MHz. The power of the ultrasonic pulse 16 is selected to ensure that the tissue 12 will not be impaired, i.e. damaged, by the injected ultrasonic energy. If possible, the ultrasonic power is selected to be low enough to prevent any heating-up of the tissue 12, in any case, however, to present cavitation effects that would destroy the tissue 12.

The system 12 further comprises ultrasound application means 24 that inject the ultrasonic pulse 16 and/or the ultrasonic pulses 16 into the tissue 12 through a tissue surface 26. The ultrasound application means 24 are configured as applicator 28 with the ultrasonic transducer 20 arranged at its distal end.

The applicator 28 is configured as an endoscope so that with the aid of the applicator 28 the ultrasonic transducer 20 can be brought up close to the tissue surface 26 of the tissue 12 under examination, even in cases where the tissue 12 is tissue in the interior of the human body, for example tissue of an organ. The applicator 28 is, however, also suited for extracorporal application of ultrasound into skin structures.

FIG. 1 shows a radiation surface 30 of the ultrasonic transducer 20, spaced from the tissue surface 26. Considering that propagation of high frequency in ultrasound is almost impossible in air, a coupling agent, for example in the form of a gel or a solid body, must be placed between the radiation surface 30 and the tissue surface 26 in cases where the radiation surface 30 cannot be brought up close to the tissue surface 26.

The system 10 further comprises ultrasound receiving means 32 for receiving the ultrasonic echo pulses reflected in the tissue 12.

When injecting the ultrasonic pulse 16, part of it is reflected at the tissue surface 26 and other tissue boundary layers, which are illustrated by way of example and are indicated by reference numerals 36, 38, 40 and 42, while part of it is permitted to pass so that an ultrasonic pulse 34 is reflected back by each of the tissue boundary layers 36, 38, 40 and 42. In the illustrated embodiment, the ultrasound receiving means 32 are formed by the same ultrasonic transducer 20 that generates the ultrasonic pulses 16, although it may of course also be envisaged to provide separate piezoelectric receivers or a waveguide. Equally, instead of providing the ultrasonic transducer 20, a waveguide may be provided through which the externally generated ultrasound is supplied to the applicator 28 which then applies it into the tissue 12.

The ultrasonic transducer 20 converts the ultrasonic echo pulse or pulses to electric pulses that are transmitted to the pulse generator 18.

The pulse generator 18 is provided with processing means 44 for ultrasonographic images, for quantitatively evaluating the ultrasonic echo pulses 34 received.

The ultrasonic echo pulses so evaluated are then supplied to a display unit 46 for being visually displayed and, if necessary, for further evaluation of the ultrasonographic image.

The components of the system 10, that have been described before and that relate to the ultrasonographic imaging process, are now combined according to the invention with components which will be described further below and with the aid of which, in combination with the ultrasonographic imaging method, an optical imaging method, or more precisely optical coherence tomography, is implemented.

With respect to the principles of optical coherence tomography and for further explanation of terms that are not explained in detail in this specification, reference is made to the overview given by Adolf F. Ferner, "Optical Coherence Tomography" in: Journal of Biomedical optics, Vol. 1, No. 2, April 1996.

The system 10 comprises for this purpose a driving and processing unit 48 for optical coherence tomography.

The driving and processing unit 48 is shown in more detail in FIG. 2.

The driving and processing unit 48 comprises initially light-generating means 50. The light-generating means 50 comprise a light source with a spectral bandwidth in the range of between 10 and 200 nm and a wavelength in the range of between 600 and 2000 nm. A light source with such spectral properties is provided, for example, by a superluminescent diode with a spectral bandwidth of 30 nm and a power of 1.5 mW.

The light generating means 50 generate at least one light beam 52, formed in the present case by a continuous sequence of light pulses; for the sake of simplicity, the light beam 52 is represented in the drawings as a single pulse.

There are further provided beam splitter means 54 by means of which the light beam 52 is split up into a reference light beam 56 and a measuring light beam 58.

The system 10 further comprises—see FIG. 1—light application means 60 for injecting the measuring light beam 58 into the tissue 12. The light application means 60 are likewise integrated in the applicator 28 and comprise a light pipe 62 constituted by a single optical fiber or an optical fiber bundle.

The light application means 60 and the ultrasound application means 24 are designed in such a way that the ultrasonic pulses 16 and the measuring light beam 58 are injected into the tissue 12 along the same beam axis 64. This makes it possible to irradiate one and the same tissue region of the tissue 12 with both ultrasound and light so that information can be derived about the tissue region, being irradiated with both ultrasound and light, from both the ultrasonographic image and the optical image obtained by optical coherence tomography.

Injection of the ultrasonic pulses 16 and the measuring light beam 58 along a common beam axis 64 is achieved with this embodiment by the fact that the light pipe 62 is likewise positioned in the applicator 58, designed as endoscope, and ends substantially centrally in the radiation surface 30 of the ultrasonic transducer 20.

The light pipe 62 further forms light receiving means 66 for receiving the measuring light beam 68 scattered back by the tissue 12, for example at the tissue boundary layers 36, 38 and/or 40.

The back-scattered measuring light beam 68 is returned to the driving and processing unit 48 via the light pipe 62. The driving and processing unit 68 further comprises means 70 for interferometrically superimposing the back-scattered measuring light beam 68 with the reference light beam 56, in order to achieve interference between the two beams. The means 70 for interferometrically superimposing the back-scattered measuring light pulse 68 and the reference light pulse 56 are formed on the one hand by the beam splitter means 54 and on the other hand by a mirror 72.

The beam splitter means 54 and the means 70 for interferometrically superimposing the back-scattered measuring light beam 68 with the reference light beam 56 are formed in the illustrated embodiment by a second-beam interferometer 74 in the form of a Michelson interferometer. The Michelson interferometer is, more exactly, only a partial Michelson interferometer since the mirror in the measuring arm, usually provided in a complete Michelson interferometer, is replaced in this case by the tissue being examined.

The beam splitter means 54 are formed in this case by a planar-parallel semitransparent glass plate being inclined relative to the direction of irradiation of the light beam 52. The second-beam interferometer 74 comprises, accordingly, a reference arm 76 and a measuring arm 78. The reference arm 76 may be adjustable in order to adjust the optical path length of the reference arm 76 relative to the optical path length of the measuring arm 78. It would, however, also be possible to make the measuring arm 78 adjustable and to adjust it in order to vary the relative optical path between the reference arm 76 and the measuring arm 78. Other possibilities include, for example, moving the object, here the tissue, relative to the measuring tissue.

Ways of implementing the adjustability of the optical path through adjustment of the optical path of the reference arm 76 include, for example, mechanically moving the mirror 72, influencing the light path of the reference light beam 56 in glass fibers via piezo elements or, without mechanical adjustment, using dispersive elements in the light path.

The driving and processing unit 48 further comprises a photodetector 80 for detecting the amplitude of the signal from the interferometric superimposition of the back-scattered measuring light beam 68 and the reference light beam 56. The photodetector 80 already comprises electric means that permit the amplitude of an interference signal to be detected, for example by deducting the DC content, rectification and averaging. The measuring signal generated by the photodetector 80 is then supplied to an amplifier 82. Finally, the amplified signal is supplied to optical image processing means 84, for processing of the interferometric measuring signal.

The optical image processing means 84 and the ultrasonographic image processing means 44 are then combined in the display unit 46.

The system 10 further comprises means—not shown in detail—for displacing the beam axis 64 in a plane parallel to the tissue surface 26, as indicated by arrows 86 and 88.

As has been mentioned before, the ultrasonic pulse or pulses 16 and the measuring light beam 58 are injected into the tissue 12 along a common beam axis 64. The ultrasonic pulses 16 injected into the tissue 12 penetrate into the tissue 12 deeper than the measuring light beam 58. On the other hand, it is possible to derive from the back-scattered measuring light beam 68 an image that offers a resolution higher by approximately the factor 10 than the ultrasonographic trace obtained by processing the ultrasonic echo pulses 34. By the combination of the ultrasonic echo pulse method and optical coherence tomography, rendered possible by the system 10, it is now possible to optimally utilize both advantages, namely on the one hand the greater depth of penetration of the ultrasound and on the other hand the higher resolution of the image obtained by optical coherence tomography.

The ultrasonographic trace and the image obtained by optical means are combined in the display unit 46 so that the optical image is displayed in the near region while the ultrasonographic trace is displayed in the far region. The image obtained by optical means permits, for example, the tissue layers between the tissue boundary layers 36 and 38 and/or 38 and 40 to be displayed with high resolution, while the ultrasonographic trace allows further information to be obtained about the tissue in the region between the tissue boundary layers 40 and 42.

The combination of the ultrasonographic image and the optical image obtained by optical coherence tomography makes it possible, for example, to determine the sound propagation speed of the tissue layer between the tissue boundary layers 36 and 38 and, thus, the thickness and elasticity of that tissue.

The upper diagram in FIG. 3 represents in this connection the image obtained by optical means, where the amplitude of the interferometric measuring signal received from the photodetector 80 has been plotted against the Y axis, while the path length along the beam axis 64 has been plotted against the X axis. It is now possible, by optical coherence tomography, to determine interferometrically the thickness d of the tissue layer between the two tissue boundary layers 36 and 38 from the distance of the measuring signal relating to the tissue boundary layer 36, which is assigned to the measuring light beam 68 scattered back at that boundary layer, and the measuring signal relating to the tissue boundary layer 38, which is assigned to the measuring light beam 68 scattered back at that layer boundary. The sequence of the measuring signals illustrated in FIG. 3 constitutes an "image" in the meaning of the invention.

The lower diagram in FIG. 3 represents the related ultrasonographic image, where the amplitude of the ultrasonic measuring signal has again been plotted against the Y axis, while the time delay of the ultrasonic echo pulse 34 has been plotted against the X axis. It is now possible to derive from that diagram the time delay difference $\tau$ between the ultrasonic echo pulse 34 reflected at the first tissue layer boundary 36 and the ultrasonic echo pulse 34 reflected at the second tissue layer boundary 38.

From the thickness d and the time delay difference $\tau$ one then obtains the sound propagation speed c in the tissue region between the tissue boundary layers 36 and 38, being $c=2d/\tau$. This analysis then permits tissue differentiation to be carried out and pathological changes in the surface structure of the tissue 12 to be detected by comparison with corresponding parameters of healthy tissue.

While the system 10, with the applicator 28 configured as endoscope, is especially suited for one-dimensional imaging, a two-dimensional ultrasonic trace/optical sectional image can also be generated by means of the system 10 by displacing the irradiation axis 46 parallel to the tissue surface 26.

FIGS. 4 to 7 show further embodiments of imaging systems according to the invention, where imaging is restricted to the region of the application systems of those imaging systems. Identical parts are indicated by the same reference numerals that have been used also for the system 10.

Figure 4:
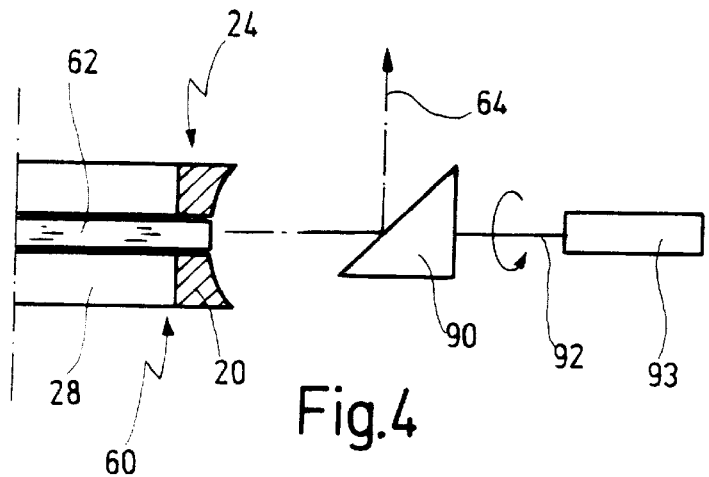
FIG. 4 shows a diagrammatic lengthwise section through another embodiment of an imaging system, in the area of the application system.

In the embodiment illustrated in FIG. 4, the ultrasound application means 24 and the light application means 60 further comprise a mirror 90 that reflects both ultrasound and light. Once the ultrasound and the light have impinged upon the mirror 90, the beam axis 64 is deflected at a right angle. The mirror 90 is further rotatable by 360° about an axis 92 extending at an angle of approximately 45° relative to the reflecting surface. This arrangement makes it possible to sweep the common beam axis 64 of the ultrasound beam and of the light beam about the rotary axis 62 extending transversely to the instantaneous direction of irradiation. This application system permits cross-sectional images of vascular wall structures of hollow organs to be obtained.

Figure 5:
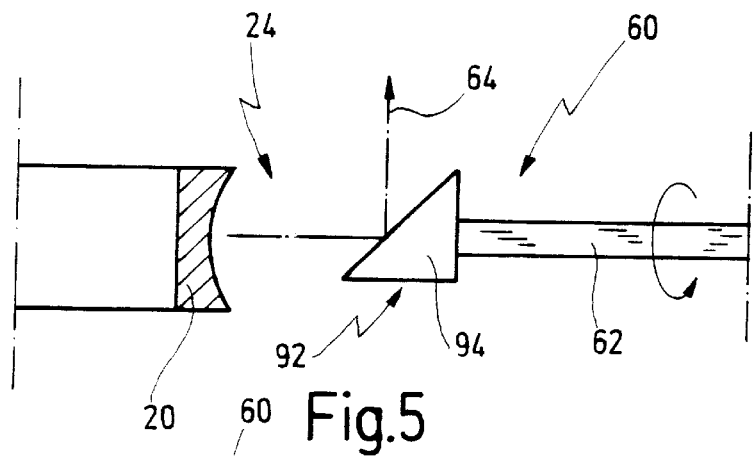
FIG. 5 shows a diagrammatic lengthwise section through another embodiment of an imaging system, in the area of the application system.

In the embodiment illustrated in FIG. 5, the light application means 60 and the ultrasound application means 24, instead of being united in a single applicator, are designed as separate units. The light application means 60 and the ultrasound application means 24 further comprise a mirror arrangement 92, comprising a mirror 94 which is inclined by 45° and which is permeable to light and reflecting to ultrasound. The mirror 94 acts again to deflect the beam axis 64 at a right angle. By rotating the mirror 64 about the axis of the light pipe 92, the beam axis 64 can again be rotated by 360° in order to generate a cross-sectional image of a hollow organ.

Figure 6:
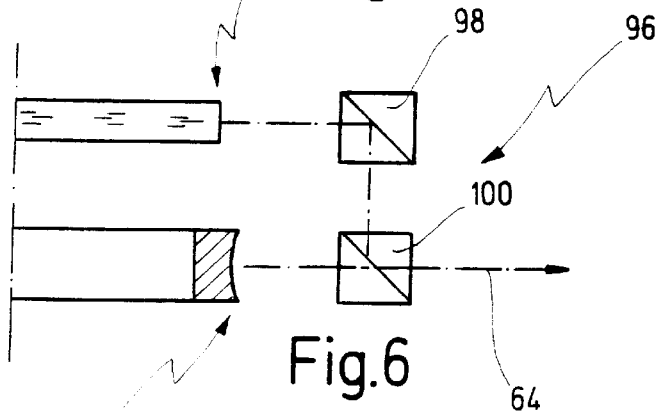
FIG. 6 shows a diagrammatic lengthwise section through another embodiment of an imaging system, in the area of the application system.

In FIG. 6, the ultrasound application means 24 and the light application means 64 are again designed as separate units. The ultrasonic beam and the measuring light beam are united, by means of a mirror arrangement 96, along the beam axis 64. The mirror arrangement 96 comprises a first mirror 98, that reflects light, and a second mirror 100 that likewise reflects light but is permeable to ultrasound.

Figure 7:
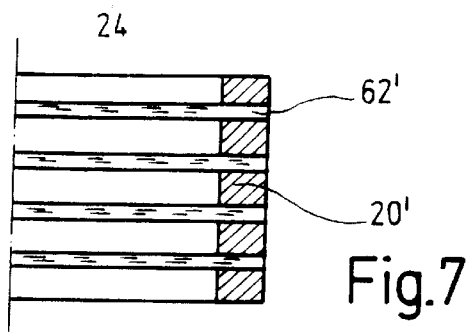
FIG. 7 shows a diagrammatic lengthwise section through yet another embodiment of an imaging system, in the area of the application system.

FIG. 7 finally shows an embodiment where the light application means 60 and the ultrasound application means 24 comprise an array of a plurality of light pipe elements 62' alternating with a plurality of ultrasonic transducer elements 20'. This configuration of the application system permits a two-dimensional sectional image to be obtained by the fact that the different array elements are driven in phase-coupled fashion at the given phase relationship. Again, ultrasound and light are directed into the tissue to be examined along a common beam axis (not shown) in a superimposed fashion. One thereby obtains an electronic scanning mechanism, instead of the mechanical scanning mechanism described with reference to FIGS. 1, 4 and 5.

What we claim is:

1. An imaging method for determining a physical or chemical condition of tissue in a human or animal body using ultrasound, comprising the steps of:
    directing at least one ultrasonic pulse in the diagnostic frequency and power range into said tissue along a beam axis;
    receiving an ultrasonic echo pulse reflected by said tissue;
    processing said ultrasonic echo pulse in ultrasonographic image processing means;
    generating at least one light beam and splitting said light beam into at least one measuring light beam and at least one reference light beam;
    directing said measuring light beam along said beam axis into said tissue, such that said ultrasonic pulse and said measuring light beam are superimposed;
    adjusting a relative optical path between said reference light beam and said measuring light beam; and
    bringing said measuring light beam scattered back by said tissue into an interference relationship with said reference light beam and processing the interferometric signal in optical image processing means.

2. The method of claim 1, wherein said light beam is generated with a spectral bandwidth in a range of between 10 and 200 nm.

3. The method of claim 1, wherein said light beam is generated in a wavelength range of between 600 and 2000 nm.

4. The method of claim 1, wherein said ultrasonic pulse is generated in a frequency range of between 1 and 200 MHz.

5. The method of claim 1, wherein said ultrasonic pulse is generated with a bandwidth in the range of between 5 and 75 MHz.

6. The method of in claim 1, wherein said relative optical path between said reference light beam and said measuring light beam is adjusted beyond one coherence length of the light.

7. The method of claim 1, wherein a sequence of ultrasonic pulses is injected into said tissue as an ultrasonic beam, said ultrasonic beam and said measuring light beam being superimposed.

8. The method of claim 7, wherein said common beam axis of said ultrasonic beam and said measuring light beam is swept in a plane parallel to a surface of said tissue.

9. The method of claim 1, wherein a sequence of ultrasonic pulses is injected into said tissue as an ultrasonic beam, said ultrasonic beam and said measuring light beam being superimposed, and wherein said common beam axis of said ultrasonic beam and of said measuring light beam is rotated about a rotary axis transversely to an instantaneous direction of irradiation.

10. The method of claim 1, wherein an image obtained optically by processing said back-scattered measuring light beam and said ultrasonographic image obtained by processing said ultrasonic echo pulse are combined one with the other such that the image optically obtained is displayed in a near range and said ultrasonographic image is displayed in a far range.

11. The method of claim 1, wherein a thickness d of a tissue layer near the surface is determined by means of said optical image obtained by processing said back-scattered measuring light beam, a difference in time delay $\tau$ between said ultrasonic echo pulse reflected at a first tissue layer boundary and said ultrasonic echo pulse reflected at a second tissue layer boundary is determined from said ultrasonographic image, and a sound propagation speed in said tissue layer is determined from a difference in said time delay $\tau$ and said thickness d.

12. The method of claim 1, wherein said ultrasonographic image is used as overview image of said tissue being examined, while said optical image is used for a detailed imaging of selected tissue regions.

13. The method of claim 1, wherein fluorescence is additionally induced in said tissue by said measuring light beam or light irradiated into the tissue independently of said light beam, and fluorescent light is received, and a fluorescent image is displayed in addition to the image optically obtained.

14. The method of claim 1, wherein it is used for tissue differentiation and/or for determining pathological changes in the surface structure of said tissue.

15. The method of claim 1, wherein it is used for visualizing dynamic processes, such as flowing blood or motions in said tissue.

16. The method of claim 1, wherein it is used for controlling a therapy of pathological tissue.

17. Imaging system for determining a physical or chemical condition of tissue in a human or animal body using ultrasound, comprising:
    ultrasound-generating means for generating at least one ultrasonic pulse in the diagnostic frequency and power range;
    ultrasound application means for applying said ultrasonic pulse into said tissue;
    ultrasound receiving means for receiving an ultrasonic echo pulse reflected by said tissue;
    ultrasonographic image processing means for processing said ultrasonic echo pulse;
    light generating means for generating at least one light beam;
    beam splitter means for splitting up said light beam into at least one measuring light beam and at least one reference light beam;
    adjusting means for adjusting a relative optical path between said measuring light beam and said reference light beam;
    light application means for applying said measuring light beam into said tissue, said light application means and said ultrasound application means being configured such that said ultrasonic pulse and said measuring light beam are superimposed and directed into said tissue along a common beam axis;

means for receiving said measuring light beam scattered back by said tissue;

means for interferometrically superimposing said back-scattered measuring light beam and said reference light beam; and optical image processing means for processing the interferometric measuring signal.

18. The system of claim 17, wherein said light-generating means comprise a light source with a spectral bandwidth in the range of between 10 and 200 nm.

19. The system of claim 17, wherein said light generating means comprise a light source for generating said light beam in a wavelength range of between 600 and 2000 nm.

20. The system of claim 17, wherein said ultrasound-generating means generate said ultrasonic pulse in a frequency range of between 1 and 200 MHz.

21. The system of claim 17, wherein said ultrasound-generating means generate said ultrasonic pulse with a bandwidth in the range of between 5 and 75 MHz.

22. The system of claim 17, wherein said ultrasound application means and said light application means are both integrated in an applicator configured as an endoscope.

23. The system of claim 22, wherein said ultrasound generation means comprise at least one piezoelectric ultrasonographic transducer and said light application means comprise at least one light guide ending substantially centrally in a radiation surface of said ultrasonic transducer.

24. The system of claim 17, wherein said light application means and said ultrasound application means comprise a mirror arrangement that is permeable to ultrasound and reflecting to light, or vice versa, in order to inject said ultrasonic pulse and said measuring light beam along said common beam axis.

25. The system of claim 17, wherein said beam splitter means and said means for interferometrically superimposing said back-scattered measuring light beam and said reference light beam comprise a single-beam or multiple-beam interferometer, preferably a Michelson interferometer.

26. The system of claim 17, wherein means for displacing said beam axis in a plane parallel to a surface of the tissue are provided.

27. The system of claim 17, wherein means for rotating said beam axis about a rotary axis transversely to an instantaneous direction of irradiation.

28. The system of claim 17, wherein said ultrasonic image processing means and said optical image processing means are coupled one with the other in such a way that said ultrasonographic image and said image optically obtained can be displayed in superimposed fashion.

29. The system of claim 17, wherein it is used for tissue differentiation and/or for determining pathological changes in the surface structure of tissue.

30. The system of claim 17, wherein it is used for visualizing dynamic processes, such as flowing blood or motions in said tissue.

31. The system of claim 17, wherein it is used for controlling a therapy of pathological tissue.

* * * * *